United States Patent
Delaney

(10) Patent No.: US 8,075,908 B2
(45) Date of Patent: Dec. 13, 2011

(54) APPARATUS AND METHOD FOR REDUCING THE OCCURRENCE OF POST-SURGICAL ADHESIONS

(75) Inventor: John P. Delaney, Minneapolis, MN (US)

(73) Assignee: Anhese LLC, Minneapolis, MN (US)

( * ) Notice: Subject to any disclaimer, the term of this patent is extended or adjusted under 35 U.S.C. 154(b) by 104 days.

(21) Appl. No.: 12/173,480

(22) Filed: Jul. 15, 2008

(65) Prior Publication Data

US 2009/0047320 A1 Feb. 19, 2009

Related U.S. Application Data

(60) Provisional application No. 60/956,560, filed on Aug. 17, 2007.

(51) Int. Cl.
*A61K 9/00* (2006.01)
*A61K 31/336* (2006.01)
*A61K 31/205* (2006.01)
*A61K 31/365* (2006.01)
*A61K 31/439* (2006.01)
*A61K 9/14* (2006.01)

(52) U.S. Cl. ........ 424/423; 514/475; 514/563; 514/473; 514/291; 424/489

(58) Field of Classification Search .................. None
See application file for complete search history.

(56) References Cited

U.S. PATENT DOCUMENTS

| | | | | |
|---|---|---|---|---|
| 2004/0087613 A1* | 5/2004 | Molmenti | ....................... | 514/291 |
| 2005/0181023 A1* | 8/2005 | Young et al. | ................... | 424/443 |

FOREIGN PATENT DOCUMENTS

| | | |
|---|---|---|
| WO | WO 2005/079704 | 9/2005 |
| WO | WO 2006/014534 | 2/2006 |

OTHER PUBLICATIONS

Hardin, Eugene, et al., eMedicine Consumer Journal, Apr. 30, 2002, vol. 3, No. 4, Copyright 2002, eMedicine.com, Inc.

Xia, Yi-Feng, et al., "Andrographolide Attentuates Inflammation by Inhibition of NF-kB Activation through Covalent Modification of Reduced Cysteine 62 of p50", The Journal of Immunology, pp. 4208-4217, Copyright 2004 by The American Associates of Immunologist, Inc.

Hidalgo, M.A., et al., "Andrographolide Interferes with Binding of Nuclear Factor-xB to DNA in HL-60-Derived Neutrophilic Cells", The British Journal of Pharmacology, 2005 (vol. 144) (No. 5) pp. 680-686, Nature Publishing Group.

Angiotech Pharmaceuticals, Inc. Presents Positive Adhibit(TM) Data at the 19th Annual European Congress of Obstetrics and Gynecology, Apr. 7, 2006. www.biospace.com.

Journal of the National Cancer Institute, vol. 93, No. 20, Oct. 17, 2001, "Rapamycin's Resurrection: A New Way to Target the Cancer Cell Cycle".

"Angiotech-Redefining Success—Surgical Adhesions", Copyright 2006, www.angiotech.com.

"Introduction—Rapamycin", www.ch.ic.ac.uk.

"Sirolimus" From Wikipedia, en.wikipedia.org.

* cited by examiner

*Primary Examiner* — Robert A Wax
*Assistant Examiner* — Danah Al-Awadi
(74) *Attorney, Agent, or Firm* — Nikolai & Mersereau, P.A.; Thomas J. Nikolai

(57) ABSTRACT

A method for inhibiting formation of adhesions following abdominal surgery which involves application of an anti-static fatty acid ethoxylated amide (Cocamide DEA) in a matrix that is placed in the peritoneal cavity at the conclusion of an abdominal surgery and which releases this anti-adhesive chemical over a predetermined time in a range from about five to seven days. Tests conducted on laboratory rats established that the method reduced the incidences of adhesions from 100 percent (100%) in a test model to near zero percent (0%) in the treated animals. In an alternative embodiment, Andrographalide was delivered through a drug pump with similar results. In still another embodiment, an effective amount of Rapamune was delivered, via a pump, into the abdominal cavity, again with similar results.

5 Claims, No Drawings

APPARATUS AND METHOD FOR REDUCING THE OCCURRENCE OF POST-SURGICAL ADHESIONS

CROSS-REFERENCE TO RELATED APPLICATION

This application claims the benefit of the filing date of provisional application Ser. No. 60/956,560, filed Aug. 17, 2007, and the contents of which are hereby incorporated by reference.

BACKGROUND OF THE INVENTION

I. Field of the Invention

This invention relates generally to the field of abdominal surgery, and more particularly to methods for reducing or substantially eliminating formation of adhesions following such abdominal surgery.

II. Discussion of the Prior Art

Abdominal adhesions are bands of fibrous tissue that cause abdominal organs to adhere to one another or to the abdominal wall. Common examples are intestine-to-intestine, and intestine-to-pelvic organs, intestine-to-abdominal wall and omentum to any of these sites. Adhesions can develop as after-effects of peritonitis, or of abdominal trauma. However, in developed countries, such adhesions most commonly result from abdominal surgical procedures during which organs are traumatized by surgical manipulations.

In most patients, post-surgical adhesions do not produce adverse consequences. In some individuals, however, constricting adhesions block the flow of contents through the intestines, a condition called intestinal obstruction. In certain instances, a segment of bowel becomes twisted around an adhesive band, thus cutting off the normal blood supply. The affected portion of the intestine becomes non-viable and may perforate. This requires emergency surgery for corrective action. In the U.S., each year about 100,000 operations are carried out to alleviate intestinal obstructions.

Once abdominal adhesions have formed, they do not resolve. Their lysis, by operation, only temporarily eliminates them. For example, when surgery is performed for adhesive intestinal obstruction caused by adhesions, adhesions routinely re-form and later cause a new intestinal obstruction in 11%-21% of such cases.

Another complication of adhesions is female infertility, secondary to blockage of fallopian tubes. Surgical attempts to solve this problem often fail because of reformation of adhesions. Furthermore, many gynecologists are of the opinion that pelvic adhesions cause pelvic pain and they operate to divide them with the intent of alleviating the pain.

Minimally invasive techniques for abdominal procedures reduce tissue handling, but even with this approach, post-operative adhesions occur in most patients. One strategy to minimize post-surgical adhesion formation might be combining minimally invasive techniques with anti-adhesion agents. At the present time, the majority of abdominal operations are still done through a large abdominal wall incision with direct exposure.

Numerous agents have been employed clinically with the hope of preventing postoperative adhesions. A few have proved partially successful in that they reduce, but do not eliminate, subsequent adhesion formation. Available products all are site specific and are not intended to solve the problem throughout the abdomen. This is a limited benefit because the locations of future adhesions are not entirely predictable.

Some of the currently used products include hyaluronic acid and/or carboxy methylcellulose. Some are fabricated as a film, others in a sponge-like configuration. They must be applied in a selected fashion directly to the surfaces of the specific organs or areas where adhesions might be expected to form or where they would be particularly troublesome, such as over the pelvic organs. Others are constituted are viscous gels which are painted on or sprayed on specific injured sites.

Examples of commercial products are as follows:

Alliance Pharmaceutical Corporation markets a product sold under the trademark, FloGel®, which is a thermal-reversible gel comprising biocompatible polyoxamers made up of polyoxyethylene and polyoxypropylene units. It has the ability to change from a liquid to a gel upon warming to body temperature. Applied in the liquid state, it will mold to tissue contours before gelling in place. Thus, FloGel® maintains contact with tissue surfaces and serves as a physical protective barrier to adhesion formation.

Absorbable fabric barriers have been developed to prevent post-surgical adhesions. A product of the Ethicon subsidiary of the Johnson & Johnson Corporation has developed a barrier fabric which it advertises under the trademark, Gynecare Interceed®, to be placed during gynecologic surgery to reduce the incidence of pelvic adhesions.

Genzyme Corporation markets a product called SEPRA-FILM® which provides a temporary physical barrier for separating potentially adhesiogenic tissue surfaces during the critical five to seven day period when adhesions generally form. The material is bio-resorbable.

There is currently an array of similar products, none of which really eliminates adhesions and all of which are site specific. Mechanical barrier agents, generally in the form of films and sponges, are the most commonly employed and most practical agents in clinical use today for preventing adhesions in the abdominal cavity. They serve to separate raw or injured areas and, hence, mechanically block adhesions from forming, but only at selected sites. Absorption occurs by enzymatic degradation and physiological uptake. The residence time in the abdomen varies according to the agent involved. The physical integrity of the film or sponge may dissipate within a day or two after operation. The continued prevention of adhesions following the disappearance of the materials may be due to residual biochemical effects of the barrier agents. Materials used in films have included polyglycolic acid, polylactic acid, oxidized cellulose, hydrophilic polyethylene glycol and sodium hyaluronate with carboxymethylcellulous. The latter agent is sold under the trademark, SEPRAFILM®. Of the various agents proposed, the bioresorbable barrier agent, SEPRAFILM®, has yield the most significant impact in the clinical setting.

SUMMARY OF THE INVENTION

In order to minimize or eliminate intra-abdominal adhesions following an operation, we have discovered that by introducing a polymeric matrix impregnated with an anti-static agent, Cocoamide DEA, into the abdominal cavity remote from the predictable adhesion sites at the time of surgery and left in place for a period of time in a range of from five to seven days, subsequent adhesion formation is inhibited and most often eliminated. It should be noted that there exist numerous identical or nearly identical anti-static agents. The matrix may comprise, but is not limited to, polyethylene, formed as a sheet, which may be passed through the abdominal wall in the same fashion as a conventional surgical drain. The polymer matrix, preferably polyethylene, slowly releases the amide antistat into the peritoneal fluid at a rate that has empirically proved to be sufficient to inhibit adhesion formation. After the five to seven days, the plastic sheet is pulled out like a drain.

Our experiments have also established that the drugs RAPAMUNE® and Andrographalide, when released from an implanted carrier pump over a period of about seven days, post surgery, also significantly reduces the formation of surgical adhesions in lab animals.

DISCUSSION OF THE PREFERRED EMBODIMENT

In carrying out the present invention, a polymeric substrate, which has been impregnated with an ethoxylated fatty acid amide, is left to reside in the abdominal cavity following surgery for a predetermined length of time. Without limitation, a sheet of the anti-static polymeric material may be rolled to form a tube-like configuration to facilitate passage through a surgically created opening in the abdominal wall, using a trocar or similar instrument as used in laparascopic surgery. A percutaneous tether can be affixed to the proximal end of the coiled substrate. In contrast to other products, the amide impregnated substrate need not be in physical contact with the organ(s) to inhibit formation of adhesions. Over time, the Cocoamide DEA diffuses from the elastomeric substrate and mixes with abdominal fluids that effectively bathe all surfaces. Without limitation, the substrate may preferably be fabricated from a sheet of polyethylene. As later explained, other materials and vehicles may be substituted as a carrier matrix for the drug without departing from the scope of the invention. Specifically, polyester or polyethylene sheets treated with the anti-static chemical can be employed. As an alternative delivery vehicle microspheres currently used as a drug delivery vehicle can be used as a slow-release media, as can gels or micelles. Polymeric micelles are nano-sized particles that are made up of polymer chains and are usually spontaneously formed by self-assembly in a liquid, generally as a result of hydrophobic or ion pair interactions between polymer segments. They typically have a so-called "core-shell" structure. The core of the micelles, which is either the hydrophobic part or the ionic part of the nano particles, can contain small molecules such as therapeutic drugs, while the shell provides interactions with the solvent to make the nano particles stable in a liquid. Additionally, other anti-adhesive agents, RAPAMUNE® or Andrographalide might be delivered by these same means for the same purpose.

Experimental Background

The efficacy of the slow release of Cocoamide DEA into the abdominal cavity in preventing adhesion formation has been confirmed in a series of experimental studies in which Sprague-Dawley female rats were used. Two experimental models were devised that both induced adhesions in 100 percent of experimental animals.

The first is termed mesh model (M). A patch of polypropylene surgical mesh, approximately 2.5 cm square is sewn into a surgically created defect in the mid-abdominal wall of a Sprague-Dawley rat.

The time, course and extent of adhesions to the mesh was determined by repeated laparoscopic observation at predetermined intervals on days 1, 3, 5, 7, 14, 28 and 150 following mesh placement. It was found that in untreated control animals, extensive adhesions were seen at day one, which then progressively covered larger areas of the mesh surface up to seven days, after which no further adhesions developed.

Another series of Sprague-Dawley female rats was subjected to the same surgical procedures, but a polyethylene plastic film impregnated with the anti-static lipid amide, 7 cm by 7 cm in size, was left in the abdomen at the end of the operation, in a position remote from the surgical mesh.

One hundred percent of the control animals developed adhesions to the prosthetic mesh. The average area covered was over 90 percent. The smallest area of coverage was 70 percent. When the anti-static impregnated plastic was placed, most of the rats developed no adhesions. In a few instances, small adhesions developed at the junction of the mesh to the abdominal wall, but did not involve the surface area of the mesh.

The second model included no foreign materials and is designated tissue model (T). This involved an identical excision of a segment of abdominal wall with simple skin closure. In this manner, the abdominal viscera were exposed to the subcutaneous tissue. The significance of these observations is that this represents a different stimulus for the adhesion process to occur with only native tissue and no foreign material.

Using this tissues "T" model, we observed the same degree of adhesion inhibition as was found in the mesh model when the anti-static polyethylene film was present.

Based on these experiments, we concluded that the presence of the plastic, impregnated with this fatty acid amide, disposed within the peritoneal space inhibited adhesions to the adhesiogenic surface, very probably by the slow release of the drug from the film matrix into and throughout the abdominal cavity.

To determine further if the anti-static plastic providing a slow release of Cocoamide DEA inhibits adhesions in general, we carried out a similar study with yet a different model of adhesion induction. This preparation is called the "sidewall model" and is the most commonly employed experimental method for studying abdominal adhesions. A small segment of peritoneum was excised and the cecum was abraded. The presence of anti-static plastic led to much reduced adhesion formation as compared to controls, again indicating that this approach is widely applicable.

Additional studies demonstratedthat untreated polyethylene film did not, by itself, alter the adhesion pattern, nor were adhesions inhibited when a dose of the anti-static agent in the liquid form was left in the abdomen at the time of mesh placement. This latter observation indicates that more prolonged exposure to the chemical agent is needed to attain the desired effects.

The present invention offers unique approaches: (1) slow release of an anti-adhesive agent, such as Cocoamide DEA, which circulates through the abdominal cavity, thus providing generalized and prolonged protection; (2) a strategy which allows removing the foreign plastic substrate after the critical time interval for adhesion formation; and (3) the use of a class of amides that have been widely employed as anti-static agents in polymer packaging material. There are fairly extensive data in this context indicating low potential for toxicity. Such amides also have antioxidant and surfactant properties which may or may not play a role in adhesion prevention. It should be further noted that this category of chemicals is employed extensively in dermatological preparations. Cocoamide is used as an anti-static agent in polyethylene film intended for the packaging of electronic components to protect against build-up of static charges. The film used in our studies was embedded with the anti-static agent Alkamide® 518 CDD (Rhodia Novecare) during the manufacturing process. This compound is a long chain aliphatic acid with diethylamide groups. The molecules align themselves with the hydrophilic amide end extending to the surface of the film and binding water molecules. The combination is electrically conductive and, therefore, anti-static. In a liquid medium, the molecules diffuse out of the surface of the polyethylene film. The experiments we have outlined herein employed small squares of such material placed in the rat's abdomen. At this time, we do not fully understand how small concentrations of the chemical, slowly released into the peritoneal cavity of rats, following operations, act to inhibit the deposit of fibrin matrices between adjacent tissue structures, the precursors of adhesions.

It is of interest to note that the anti-static films removed after seven days in the rat abdomen, resterilized and used in a fresh M model rat yielded results identical to controls, that is, no effect on adhesions. Five such "used" films were submitted to the manufacturer where electrical assessments were made, namely, electrostatic decay rate (charged dissipation) and electrical resistance. These measurements indicated no residual anti-static properties. The anti-stat agent became fully dissipated over these seven days that the film remained in the rat's abdomen.

Next, we studied the results in the two models of infusing over a seven day period post surgery, a comparable dose of Cocamide DEA by means of a miniature pump left in the abdominal cavity. The results were virtually identical to those obtained with the anti-static polyethylene film, that is, near total elimination of adhesions in both models, M and T. It should be noted that the two methods each involved the presence of foreign material in the abdomen, polyethylene film or the cellulose casing of the pump. There seems to be a synergistic effect.

An additional unrelated chemical, Andrographalide, was tested for adhesion inhibition in the two models. Delivered by means of the intra-abdominal miniature pump over the course of a week after operation, this yielded adhesion reduction comparable to the anti-static film and to the infused alkamide.

Andrographalide is an irreversible blocker of NF-kB derived from a medicinal plant andrographis panniculata. It has wide ranging pharmacologic action including anti-oxidant and anti-inflammatory capabilities. Most pertinent to present consideration is its anti-coagulant properties, based on inhibition of tissue factor and thereby of the alternate pathway for extravascular coagulation, an essential step for adhesion formation.

A third agent has proved to generate similar anti-adhesive effects in the same rat models. RAPAMUNE® is a complex mixture prepared for oral administration to prevent rejection of transplanted organs or tissues. The mixture includes Rapamycin, Phosal® 50PG, polysorbate 80 and polyethylene glycol. We have observed that this preparation infused into the abdomen for seven days following operation serves as a powerful adhesion inhibitor in the models M and T. Rapamycin, by itself, was found not to have this effect. We also plan to explore the possible synergistic effect of using a tube of the anti-static film as an avenue for infusing the three agents individually and in combination. This strategy might permit a much reduced amount of the plastic film in the abdomen. The quantity of film needed for the full effect in the rat, if translated, weight for weight to the human would not be practical.

While not fully understood, the effects of anti-static polyethylene film might be exerted as an electrical phenomenon, possibly by attracting and inactivating platelets and thus the initial clotting process. Attempts have been made to amplify this process by applying a small electrical current to an intra-abdominal film strip, which serves as a conductive medium.

Another device now under investigation for drug delivery comprises bundles of hollow semi-permeable cellulose based microtubules of the type employed in blood oxygenators or in renal dialysis apparatuses. The agent is delivered from an external pump through the fibers or, alternatively, is loaded into the lumens of the fibers from which it slowly diffuses out of the bundle's static column.

This invention has been described herein in considerable detail in order to comply with the patent statutes and to provide those skilled in the art with the information needed to apply the novel principles and to construct and use such specialized components as are required. However, it is to be understood that the invention can be carried out by specifically different equipment and devices, and that various modifications, both as to the equipment and operating procedures, can be accomplished without departing from the scope of the invention itself.

What is claimed is:

1. A method of inhibiting formation of adhesions, post surgery, which comprises delivering an effective amount of a mixture of rapamycin in solution of at least 50% phosphatidylcholine, lecithin in propylene glycol, sunflower mono-diglycerides, ascorbyl palmitate, propylene glycol, polysorbate 80, and 1.5%-2.5% ethanol into the abdominal cavity over a predetermined time interval.

2. The method of claim 1 wherein the mixture of rapamycin in solution of at least 50% phosphatidylcholine, lecithin in propylene glycol, sunflower mono-diglycerides, ascorbyl palmitate, propylene glycol, polysorbate 80, and 1.5%-2.5% ethanol is delivered by elution from a slow release substrate and the predetermined time interval is no less than five days.

3. The method of claim 2 wherein the predetermined time period is at least seven days.

4. The method of claim 1 wherein the mixture of rapamycin in solution of at least 50% phosphatidylcholine, lecithin in propylene glycol, sunflower mono-diglycerides, ascorbyl palmitate, propylene glycol, polysorbate 80, and 1.5%-2.5% ethanol is delivered through the lumens of a bundle of tubular microfibers formed from semi-permeable membranous material.

5. A composition suitable for local, non-systemic administration of a drug topically to tissue within a body cavity having been subjected to a surgical procedure, said composition comprising a mixture of rapamycin in a solution of at least 50% phosphatidylcoline, lecithin in propylene glycol, sunflower mono-diglycerides, ascorbyl palmitate, polysorbate 80 and 1.5%-2.5% ethanol as an anti-adhesive agent in an amount effective to inhibit formation of post-operative adhesions upon local, non-systemic administration of said anti-adhesive agent to said tissue, and a carrier suitable for local prolonged administration of said anti-adhesive agent with minimal systemic circulation where the carrier is selected from a group consisting of microspheres, nanospheres, fibers, polymeric films, gel micelles and drug delivery pumps.

* * * * *